US010238765B2

(12) United States Patent
Cheng et al.

(10) Patent No.: US 10,238,765 B2
(45) Date of Patent: Mar. 26, 2019

(54) PHOTOCATALYTIC HONEYCOMB ASSEMBLY AND PHOTOCATALYTIC PURIFICATION APPARATUS

(71) Applicants: COMMERCIAL AIRCRAFT CORPORATION OF CHINA, LTD., Shanghai (CN); SHANGHAI AIRCRAFT DESIGN AND RESEARCH INSTITUTE OF COMMERCIAL AIRCRAFT CORPORATION OF CHINA, Shanghai (CN)

(72) Inventors: Zhan Cheng, Shanghai (CN); Qiaosheng Shi, Shanghai (CN); Wei Kuang, Shanghai (CN); Cun Zhang, Shanghai (CN); Zhongyuan Ren, Shanghai (CN); Guangwen Wang, Shanghai (CN); Xizhong Jian, Shanghai (CN); Chengyun Wu, Shanghai (CN); Xuede Sun, Shanghai (CN); Na Jiang, Shanghai (CN); Zhi Yang, Shanghai (CN)

(73) Assignees: COMMERCIAL AIRCRAFT CORPORATION OF CHINA, LTD., Shanghai (CN); SHANGHAI AIRCRAFT DESIGN AND RESEARCH INSTITUTE OF COMMERCIAL AIRCRAFT CORPORATION OF CHINA, Shanghai (CN)

( * ) Notice: Subject to any disclaimer, the term of this patent is extended or adjusted under 35 U.S.C. 154(b) by 0 days.

(21) Appl. No.: 15/578,224

(22) PCT Filed: Nov. 9, 2016

(86) PCT No.: PCT/CN2016/105144
§ 371 (c)(1),
(2) Date: Nov. 29, 2017

(87) PCT Pub. No.: WO2017/101619
PCT Pub. Date: Jun. 22, 2017

(65) Prior Publication Data
US 2018/0147313 A1    May 31, 2018

(30) Foreign Application Priority Data
Dec. 18, 2015    (CN) .......................... 2015 1 0960268

(51) Int. Cl.
*A61L 9/20*    (2006.01)
*A61L 9/18*    (2006.01)
(Continued)

(52) U.S. Cl.
CPC ................. *A61L 9/205* (2013.01); *A61L 9/18* (2013.01); *A61L 9/20* (2013.01); *B01D 53/86* (2013.01);
(Continued)

(58) Field of Classification Search
CPC ...................................................... A61L 2/205
See application file for complete search history.

(56) References Cited

U.S. PATENT DOCUMENTS

| 2002/0081246 A1 | 6/2002 | Tsukada et al. |
| 2005/0284137 A1 | 12/2005 | Son |

FOREIGN PATENT DOCUMENTS

| CN | 1185756 A | 6/1998 |
| CN | 1917966 A | 2/2007 |

(Continued)

OTHER PUBLICATIONS

PCT ISR and Written Opinion dated Dec. 30, 2016 from corresponding International Application No. PCT/Cn2016/105144 (12 pages).

(Continued)

*Primary Examiner* — Donald R Spamer
(74) *Attorney, Agent, or Firm* — Maier & Maier, PLLC

(57) ABSTRACT

A photocatalytic honeycomb assembly and a photocatalytic purification apparatus, which can maximally increase a (Continued)

contact area between polluted air and a photocatalyst while maximally ensuring that the surface of the photocatalyst receives sufficient irradiation of ultraviolet light, and can also make the flow resistance to air flowing in a channel meet requirements in the field of ventilation systems which have high requirements on flow resistance. The photocatalytic honeycomb assembly is formed of one or more photocatalytic honeycomb cores and a photocatalytic honeycomb assembly housing. The one or more photocatalytic honeycomb cores are arranged in a honeycomb form. The photocatalytic honeycomb core is formed of three or more basic core units and a light guide member that is Y-shaped in an end view.

11 Claims, 15 Drawing Sheets

(51) Int. Cl.

| | | |
|---|---|---|
| *B01D 53/86* | (2006.01) | |
| *B01D 53/88* | (2006.01) | |
| *F24F 3/16* | (2006.01) | |
| *B01J 35/00* | (2006.01) | |
| *B01J 35/04* | (2006.01) | |
| *B60H 3/00* | (2006.01) | |

(52) U.S. Cl.
CPC ......... *B01D 53/8687* (2013.01); *B01D 53/88* (2013.01); *B01D 53/885* (2013.01); *B01J 35/004* (2013.01); *B01J 35/04* (2013.01); *F24F 3/16* (2013.01); *B01D 2255/20707* (2013.01); *B01D 2255/802* (2013.01); *B60H 3/00* (2013.01)

(56) References Cited

FOREIGN PATENT DOCUMENTS

| | | |
|---|---|---|
| CN | 105396459 A | 3/2016 |
| CN | 105423438 A | 3/2016 |
| CN | 105435290 A | 3/2016 |
| JP | 2004016832 A | 1/2004 |
| JP | 2010227840 A | 10/2010 |
| WO | 9817390 A2 | 4/1998 |
| WO | 2008105295 A1 | 9/2008 |
| WO | 2014156294 A1 | 10/2014 |

OTHER PUBLICATIONS

State Intellectual Property Office (SIPO) First Office Action dated Jun. 2, 2017 from corresponding Chinese Application No. 201510960268.4 with English version (10 pages).
State Intellectual Property Office (SIPO) Notice of Allowance dated Aug. 4, 2017 from corresponding Chinese Application No. 201510960268.4 with English version ( 6pages).

PHOTOCATALYTIC HONEYCOMB ASSEMBLY AND PHOTOCATALYTIC PURIFICATION APPARATUS

FIELD

The present invention relates to a photocatalytic honeycomb assembly and a photocatalytic purification apparatus, and more particularly, to a photocatalytic purification apparatus that purifies air by using the principle of photocatalysis and a photocatalytic honeycomb assembly that is provided in the photocatalytic purification apparatus.

BACKGROUND

A photocatalyst is a substance that makes a chemical reaction happen more quickly under light irradiation without being changed itself. Under light irradiation, the photocatalyst can activate adsorbed oxygen and moisture on the surface of a material, thereby producing free hydroxy groups and active oxygen that have a very strong oxidizing ability and setting off an oxidation reaction, so as to completely decompose organic matter, bacteria, viruses, etc. into carbon dioxide and water.

The photocatalytic air purification technology is currently an ideal technology internationally acknowledged for treatment of environmental pollutants. The key to a desirable photocatalytic purification effect is to further enlarge a contact area between polluted air and a photocatalyst and further ensure that the surface of the photocatalyst receives sufficient light irradiation. Moreover, in addition to a photocatalyst that is activated by irradiation of ultraviolet light, the photocatalyst may alternatively be a photocatalyst that is activated by irradiation of other light (for example, visible light).

In addition, existing photocatalytic purification apparatuses are mainly classified according to structures into the following types of a single-channel type, a single-channel surface-extended type, a honeycomb-channel stacked type, and a light-source-extended type. Each type of apparatus is described below in brief.

(1) Single-channel Type

A single-channel structure is a typical structure of a photocatalyst apparatus. A single-channel photocatalyst apparatus comprises only one channel. A photocatalyst coating is applied to a wall surface of the channel. An ultraviolet lamp is disposed at the centre of the channel. A photocatalyst is activated to set off a photocatalytic oxidation reaction.

JIN Ning et al. from University of Shanghai for Science and Technology researched an apparatus that integrates pre-filtration, high-efficiency filtration, active carbon filtration and photocatalytic filtration. The structure of such an integrated apparatus 1A is shown in FIG. 1. Air enters the apparatus through a sidewall 10A1 of a cylindrical barrel 10A. Under the action of a fan 20A disposed inside, the air sequentially passes through multiple filter meshes (a pre-filter mesh 30A, a high-efficiency particulate air (HEPA) filter mesh 40A, and an active carbon filter mesh 50A) to reach an internal filter mesh 60A with $TiO_2$ (a photocatalyst) attached thereto. A double-tube ultraviolet lamp 70A is disposed at the centre of the cylindrical barrel 10A of the integrated apparatus 1A. Therefore, when the photocatalyst is in an activated state and polluted air passes through the photocatalyst, a redox reaction occurs. In this way, an air purification process is implemented as a whole by multi-filtration.

However, as shown in FIG. 1, the single-channel type has a disadvantage of a small contact area between polluted air and the photocatalyst ($TiO_2$). Therefore, a reaction area where the reaction takes place is also relatively small.

(2) Single-channel Surface-extended Type

As discussed above, because a single-channel photocatalyst apparatus has a relatively small reaction area, to increase a reaction area between polluted air and a photocatalyst, a single-channel surface-extended structure is proposed. The single-channel surface-extended structure is based on the single-channel structure and replaces the simple wall surface of a channel with a carrier in other forms as an attachment surface for a photocatalyst. In such a manner, a surface area of the photocatalyst is increased, and thus the reaction efficiency of the apparatus can be improved.

YAN Qinian et al. researched a photocatalyst apparatus in a guided convoluted air-channel form. The structure of such a photocatalyst apparatus 1B in a guided convoluted air-channel form is shown in FIG. 2. Compared with the single-channel photocatalyst apparatus, such a photocatalyst apparatus 1B in the form of a guided convoluted air-channel has a separator plate (not shown) to form a spiral channel 20B. A $TiO_2$ coating (a photocatalyst coating) is sprayed onto a pipe wall 11B and is also sprayed and attached onto the separator plate, thereby increasing a reaction area. Four (only two are shown here) ultraviolet lamp tubes 31A and 32A having different radiation wavelengths are disposed in a central-axis direction of the apparatus. In this way, a resonant light source is formed, to enable a photocatalyst to be in a high-intensity activated state. In the photocatalyst apparatus 1B in a guided convoluted air-channel form shown in FIG. 2, since both the length of the channel and a coating area are considerably extended, the two factors also become the key to the improvement of reaction efficiency.

In addition, ZHAO Gang designed a mesh-type photocatalyst apparatus for passenger trains, and the structure thereof is shown in FIG. 3. Such a mesh-type photocatalyst apparatus 1C is installed on an air return pipe (not shown) and is of a flat drawer-form structure. A distance between an outlet and an inlet of a channel is relatively small, and two end surfaces are each provided with a metal mesh structure. A $TiO_2$ coating (a photocatalyst coating) is attached to the mesh, and is brought into an activated state after being irradiated by two ultraviolet lamp tubes 10C disposed in the middle of the channel. Because of a special shape requirement of this apparatus, the coating of the apparatus is disposed in a direction perpendicular to the channel. Further, to prevent the channel from being blocked, a mesh structure is used. However, the mesh structure does not extend an area as much as expected, which is not an ideal carrier form. As a result, the efficiency of a single-pass reaction of the apparatus is relatively low. Therefore, the structure of the mesh photocatalyst apparatus 1C shown in FIG. 3 is applicable only to a case in which air can repeatedly return and the concentration of polluted air is relatively low.

In addition, SHAN Xinggang et al. conducted experimental research on photocatalysis. An experimental apparatus used in the research is a structural form of a glass sleeve. An ultraviolet lamp tube is installed in an inner quartz tube, and small glass beads are filled in the outer glass sleeve. $TiO_2$ (a photocatalyst) is sprayed and attached onto the small glass beads in a coating form, so as to form a packed bed. In this way, a reaction area can be greatly extended.

However, the single-channel surface-extended photocatalyst apparatuses in the foregoing three cases all have the following disadvantage: air flowing in the channel is subject to relatively large flow resistance, which probably cannot satisfy flow resistance requirements in the field of ventilation systems that are relatively sensitive to flow resistance, for example, a ventilation system for a vehicle.

(3) Honeycomb-channel Stacked Type

Similar to a surface-extended structure, the honeycomb channel structure is proposed to increase a reaction surface. However, because honeycomb channels are distributed intensively and an ultraviolet source cannot be disposed inside each channel, an ultraviolet lamp tube can only be placed at inlets and outlets of the channels. In addition, in consideration of a limited irradiation range of light rays, the channels cannot be configured to be excessively long. Therefore, a honeycomb-channel stacked structure emerges, in which relatively short honeycomb channel structures and ultraviolet lamps are stacked.

A photocatalyst apparatus 1D designed for a passenger cabin by WANG Jun's research group from Beihang University is exactly of such a honeycomb-channel stacked structure. The structure thereof is shown in FIG. 4. The reason for using a honeycomb channel is that, as compared with structures such as in the form of a packed bed and a metal mesh shown in FIG. 3, a honeycomb channel structure has much lower flow resistance. In addition, a $TiO_2$ coating (a photocatalyst coating) 30D is sprayed and attached onto a wall surface of each honeycomb channel 10D. A stacked structure of multiple groups of ultraviolet lamps 20D and honeycomb channels 10D is used, such that most of the honeycomb channels 10D are in desirable conditions of ultraviolet light irradiation. In this way, considerably high reaction efficiency can be achieved.

In addition, LU Yuanwei et al. also researched such a honeycomb-channel stacked structure. A honeycomb channel board used has a size of 300 mm×300 mm, a thickness of 6 mm, and a honeycomb cell density of 250×250 unit/$m^2$. Through calculation and verification, it is found in the research that an optimal aspect ratio of a honeycomb channel is 1.5. With this structural ratio, it can be ensured that light intensity is fully used. In addition, GU Changjun et al. also researched such a structure. Different from that of LU Yuanwei et al., GU Changjun et al. used a ceramic mesh in place of a metal mesh and also achieved a desirable experimental effect.

However, the honeycomb-channel stacked photocatalyst apparatuses in the foregoing three cases also have the following disadvantage: air flowing in the channels is subject to relatively large flow resistance, which probably cannot satisfy flow resistance requirements in the field of ventilation systems that are relatively sensitive to flow resistance, for example, a ventilation system for a vehicle.

(4) Light-source-extended Type

In addition to the foregoing photocatalyst apparatuses of relatively conventional types, some other researchers tried some unconventional ways, and extended light paths to make light intensity distribution more uniform, so as to improve reaction efficiency.

FENG Qiaolian et al. proposed a concept of using optical fibres as extended light sources. A photocatalyst apparatus 1E conceived of by FENG Qiaolian et al. is shown in FIG. 5. Optical fibres LF replace blades of a fan BL and are inserted in a hub H of the fan BL. A $TiO_2$ coating covers the surface of the optical fibres LF. An ultraviolet lamp tube 20E is disposed at the centre of the hub, and optical fibre bundles distributed in a radial direction can extend ultraviolet sources to a coating part, so as to activate a photocatalyst to set off a photocatalytic reaction. However, this concept has not been physically implemented yet, and the actual effect of the concept is still to be verified.

YE Jianren proposed a carrier in which $SiO_2$ is used as a photocatalyst. A photocatalyst apparatus 1F produced by YE Jianren is shown in FIG. 6. In an experiment, a three-dimensional skeleton made of $SiO_2$ needs to be prepared first, a $TiO_2$ coating is then attached to the skeleton, and the skeleton is placed inside the apparatus in the form of a packed bed. An ultraviolet lamp tube is disposed near the carrier. Since a light path may be extended for a light source by using $SiO_2$, a photocatalyst in such a form is also of a light-source-extended type, being significantly conducive to improvement of reaction efficiency.

As may be known from the foregoing description, there is still no such a photocatalytic apparatus that can maximally increase a contact area between polluted air and a photocatalyst, as well as maximally ensure that the surface of the photocatalyst receives sufficient irradiation of light, and can also make the flow resistance to air flowing in a channel meet requirements in the field of ventilation systems that are demanding on flow resistance, for example, the field of airplane ventilation system design. Therefore, how to design a photocatalytic apparatus that can satisfy all these conditions becomes a technical problem that urgently needs to be resolved.

SUMMARY

To resolve the foregoing technical problem, the objective of the present invention is to provide a photocatalytic honeycomb assembly and a photocatalytic purification apparatus. The application of the photocatalytic honeycomb assembly and the photocatalytic purification apparatus can maximally increase a contact area between polluted air and a photocatalyst, as well as maximally ensure that the surface of the photocatalyst receives sufficient irradiation of light, and can also make the flow resistance to air flowing in a channel meet requirements in the field of ventilation systems that are demanding on flow resistance.

To achieve the foregoing objective of the invention, a first technical solution of a first aspect of the present invention provides a photocatalytic honeycomb assembly, comprising a photocatalytic honeycomb assembly housing and one or more photocatalytic honeycomb cores, the photocatalytic honeycomb core being formed of three or more basic core units and a light guide member which are arranged in a honeycomb form, the light guide member being Y-shaped in an end view and being disposed between every three basic core units that are adjacent to one another, among the three basic core units that are adjacent to one another, a first basic core unit and a second basic core unit sharing a first light guide plate, the first basic core unit and a third basic core unit sharing a second light guide plate, and the second basic core unit and the third basic core unit sharing a third light guide plate, each basic core unit being in a form of a honeycomb air channel that is formed of four coated surfaces and two light guide surfaces of the light guide plates and able to allow air to flow therethrough, and the first light guide plate, the second light guide plate and the third light guide plate forming the light guide member that is able to guide light emitted by a light source into the honeycomb air channels.

By using the structure discussed above, the light guide plates of the light guide member can be used to guide light (for example, ultraviolet light or visible light) emitted by the light source to the honeycomb air channel of the basic core unit. In this way, not only a contact area between polluted air and a photocatalyst can be maximally increased, but also it can be maximally ensured that the surface of the photocatalyst receives sufficient light irradiation. In addition, a manner of disposing a photocatalyst coating in the honeycomb air channel is used, so that flow resistance to air can be reduced, and pressure loss of equipment is relatively small.

A photocatalytic honeycomb assembly of a second technical solution of the first aspect of the present invention is based on the photocatalytic honeycomb assembly of the first technical solution of the first aspect of the present invention, wherein a photocatalyst coating is sprayed and attached onto the four coated surfaces of each basic core unit.

By using the structure discussed above, the photocatalyst coating sprayed and attached onto the coated surface of each basic core unit can receive uniform light irradiation to enable a uniform and ideal photocatalytic purification reaction.

A photocatalytic honeycomb assembly of a third technical solution of the first aspect of the present invention is based on the photocatalytic honeycomb assembly of the first technical solution of the first aspect of the present invention, wherein a light source is disposed on an end surface of each light guide plate of the light guide member that is Y-shaped in an end view, and the light source extends along an axial length of the photocatalytic honeycomb core and is configured inside the light guide plate.

By using the structure discussed above, the light guide plates can be used to transform the light source into a surface light source facing the honeycomb air channel of the basic core unit, so that the problem that light irradiation cannot go deep into the photocatalytic honeycomb core in the photocatalytic honeycomb assembly can be resolved.

A photocatalytic honeycomb assembly of a fourth technical solution of the first aspect of the present invention is based on the photocatalytic honeycomb assembly of the third technical solution of the first aspect of the present invention, wherein the light source disposed on each light guide plate of the light guide member is a row of multiple dot-matrix light sources or strip light sources.

A photocatalytic honeycomb assembly of a fifth technical solution of the first aspect of the present invention is based on the photocatalytic honeycomb assembly of the first technical solution of the first aspect of the present invention, wherein the four coated surfaces of the basic core unit are divided at regular intervals along a circumferential direction of the photocatalytic honeycomb core, so as to divide each of the coated surfaces into multiple rectangular alternately disposed regions having equal areas that are adjacent to one another both in the axial direction and the circumferential direction, different coatings, i.e. photocatalyst coatings and specular reflection coatings, are alternately sprayed and attached onto the alternately disposed regions that are adjacent in the axial direction.

By using the structure discussed above, each coated surface is equally divided into multiple alternately disposed rectangular regions that are adjacent in the axial direction and adjacent in the circumferential direction and have equal areas, wherein different coatings, that is, a photocatalyst coating and a specular reflection coating, are alternately sprayed and attached to the alternately disposed regions that are adjacent in the axial direction. Therefore, in the honeycomb air channel, light (for example, ultraviolet light or visible light) emitted by a point light source, a light strip, etc. disposed inside a side casing is reflected inside the photocatalytic honeycomb core by the specular reflection coating along the axial direction of the photocatalytic honeycomb assembly. In this way, ultraviolet light can be irradiated to even a position in the center of the honeycomb air channel of the photocatalytic honeycomb core that has a long axial length.

In this way, the specular reflection coating can alternately reflect ultraviolet light emitted by point light sources, ultraviolet strips, etc. that are disposed on the side casing on two sides of the photocatalytic honeycomb core into the honeycomb air channel. The photocatalyst coating is irradiated by ultraviolet light that is reflected one or more times by the specular reflection coating, so that a photocatalyst is activated to decompose organic matter, bacteria, viruses, etc. contained in polluted air into carbon dioxide and water, that is, to purify the polluted air.

A photocatalytic honeycomb assembly of a sixth technical solution of the first aspect of the present invention is based on the photocatalytic honeycomb assembly of the fifth technical solution of the first aspect of the present invention, wherein different coatings, i.e. photocatalyst coatings or specular reflection coatings, are also alternately sprayed and attached onto the alternately disposed regions that are adjacent in the circumferential direction.

By using the structure discussed above, because different coatings, that is, a photocatalyst coating and a specular reflection coating, are also alternately sprayed and attached to the alternately disposed regions that are adjacent in the circumferential direction, light (for example, ultraviolet light or visible light) emitted by point light sources, light strips, etc. that are disposed inside the side casing can be reflected more uniformly inside the photocatalytic honeycomb core, so as to avoid a case in which the catalytic efficiency of some photocatalyst coatings inside the photocatalytic honeycomb core is significantly reduced as compared with the catalytic efficiency of photocatalyst coatings in other parts.

A photocatalytic honeycomb assembly of a seventh technical solution of the first aspect of the present invention is based on the photocatalytic honeycomb assembly of the first technical solution of the first aspect of the present invention, wherein a photocatalyst coating is sprayed and attached onto one, two or three of the four coated surfaces of each basic core unit, and a specular reflection coating is sprayed and attached on the remaining coated surface(s).

By using the structure discussed above, not only the light guide member is used to transform light emitted by light sources into a surface light source facing the honeycomb air channel of the basic core unit, but also the specular reflection coating can be used to make light irradiation of the honeycomb air channel of the basic core unit more uniform.

A first technical solution of a second aspect of the present invention provides a photocatalytic purification apparatus, wherein the photocatalytic purification apparatus is comprised of a photocatalytic honeycomb assembly of any one of the first technical solution to the fourth technical solution of the first aspect of the present invention, a side casing, an air vent inlet pipe and an air vent outlet pipe, and one or more light sources able to emit light are disposed on an inner side surface of the side casing.

By means of the structure as discussed above, the photocatalytic purification apparatus having the foregoing photocatalytic honeycomb assembly can maximally increase a contact area between polluted air and a photocatalyst, as well as maximally ensure that the surface of the photocatalyst receives sufficient irradiation of ultraviolet light, and can also make the flow resistance to air flowing in a channel meet requirements in the field of ventilation systems that are demanding on flow resistance.

A photocatalytic purification apparatus of a second technical solution of the second aspect of the present invention is based on the photocatalytic purification apparatus of the first technical solution of the second aspect of the present invention, wherein the multiple light sources are multiple LED point light sources that are arranged on the inner side surface of the side casing in the form of concentric circles, and light emitted from the multiple LED point light sources is irradiated into the photocatalytic honeycomb core in the photocatalytic honeycomb assembly.

A photocatalytic purification apparatus of a third technical solution of the second aspect of the present invention is based on the photocatalytic purification apparatus of the first technical solution of the second aspect of the present invention, wherein the multiple light sources are multiple light strips that are arranged on the inner side surface of the side casing in the form of concentric circles, and light emitted from the multiple light strips is irradiated into the photocatalytic honeycomb core in the photocatalytic honeycomb assembly.

A photocatalytic purification apparatus of a fourth technical solution of the second aspect of the present invention is based on the photocatalytic purification apparatus of the second technical solution or the third technical solution of the second aspect of the present invention, wherein a first light source section or a first light strip located on the inner surface on one end side of the side casing has the lowest light intensity, and a third light source section or a third light strip located on the inner surface on the other end side of the side casing has the highest light intensity, in a high purification mode, the first light source section or first light strip, a second light source section or second light strip, and the third light source section or third light strip are all turned on, in a medium purification mode, the first light source section or first light strip and the second light source section or second light strip are turned on, and in a low purification mode, only the first light source section or first light strip is turned on.

By using the structure discussed above, light (for example, ultraviolet light or visible light) emitted by light sources with different intensity can be used to meet purification requirements of different processing demands.

DETAILED DESCRIPTION OF THE DRAWINGS

A photocatalytic honeycomb assembly 100 and a photocatalytic purification apparatus 10 having the photocatalytic honeycomb assembly 100 according to the present invention are described below with reference to the accompanying drawings.

(Overall Structure of the Photocatalytic Purification Apparatus 10)

Figure 1:
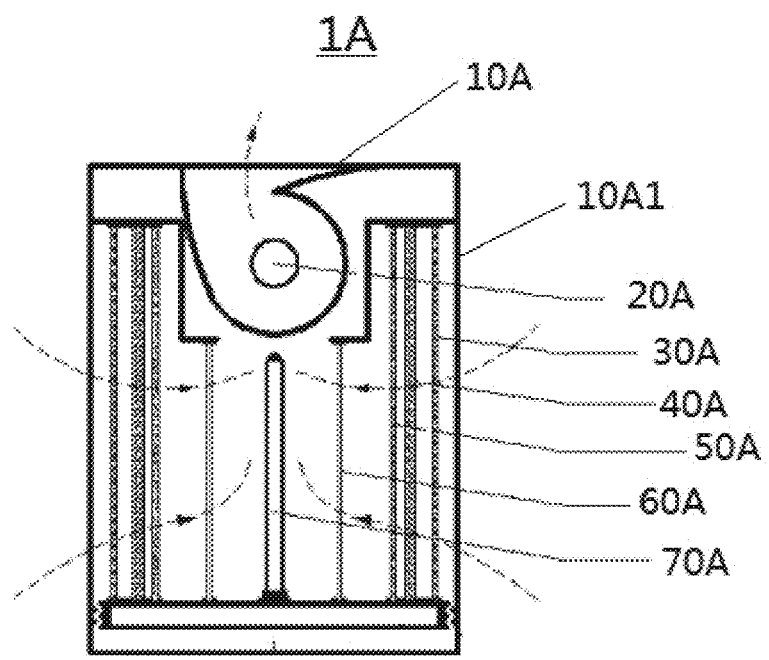
FIG. 1 is a schematic diagram illustrating a single-channel photocatalytic purification apparatus in the prior art.
Figure 2:
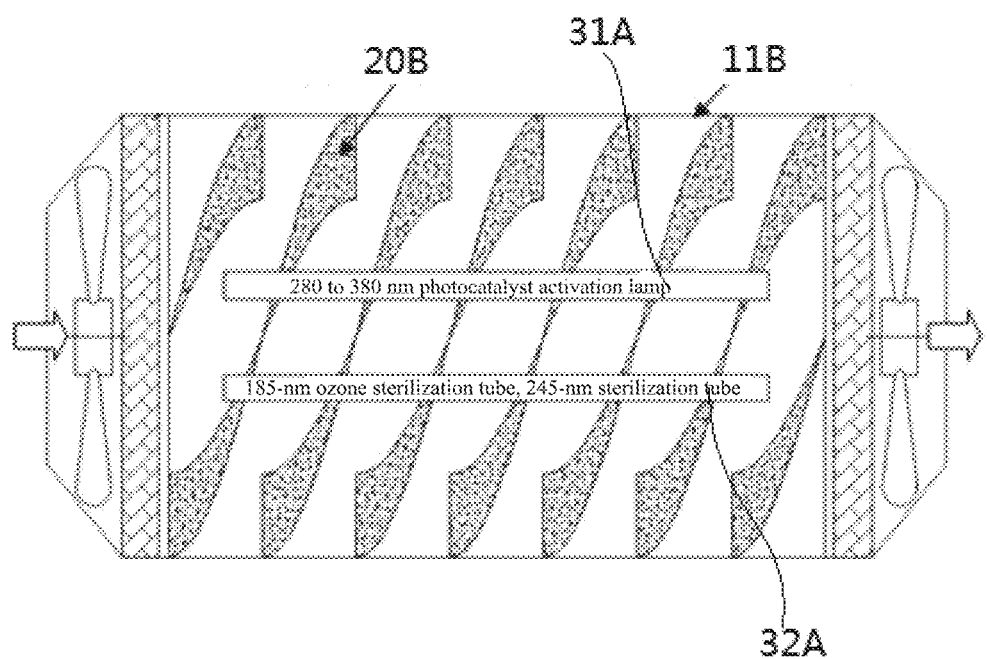
FIG. 2 is a schematic diagram illustrating a photocatalyst apparatus of a single-channel surface-extended type (in a guided convoluted air-channel form) in the prior art.
Figure 3:
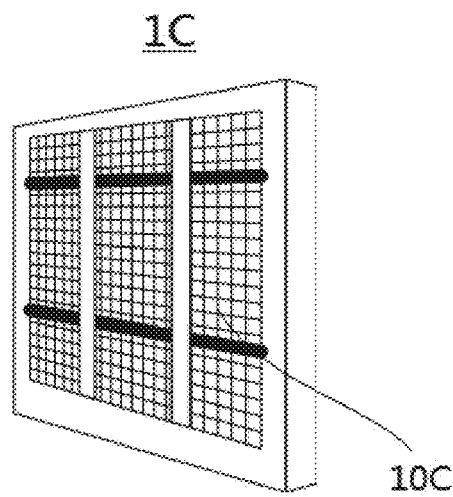
FIG. 3 is a schematic diagram illustrating another photocatalyst apparatus of a single-channel surface-extended type (mesh type) in the prior art.
Figure 4:
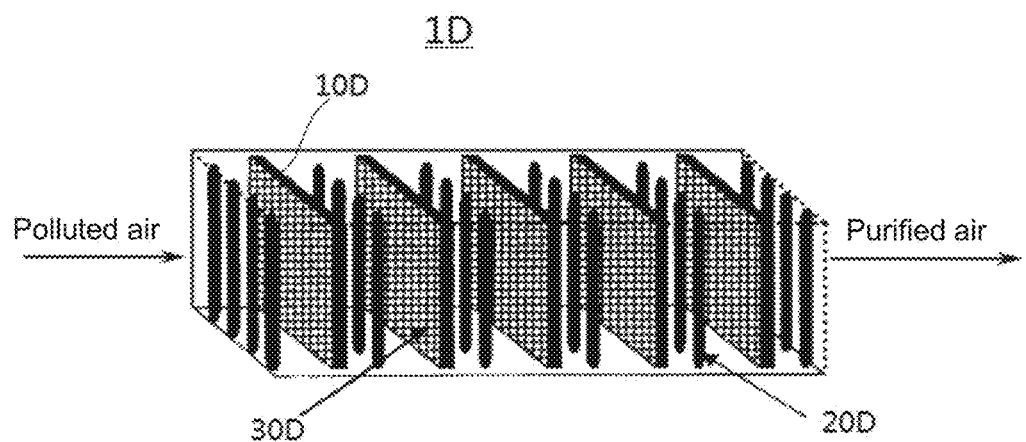
FIG. 4 is a schematic diagram illustrating a photocatalyst apparatus of a honeycomb-channel stacked type in the prior art.
Figure 5:
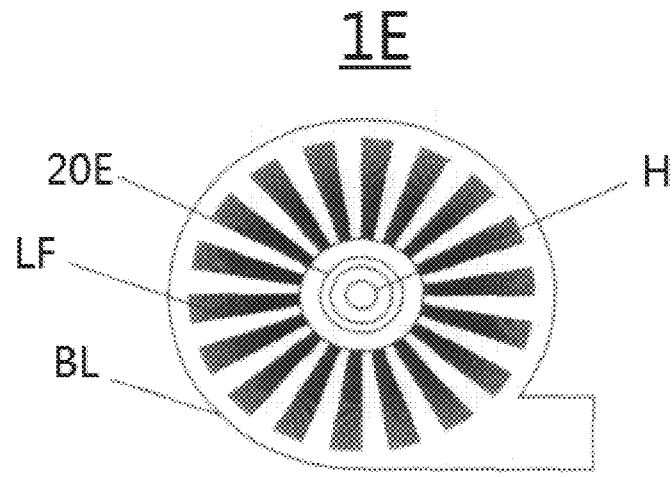
FIG. 5 is a schematic diagram illustrating a photocatalyst apparatus of a light-source-extended type (using optical fibres as extended light sources) in the prior art.
Figure 6:
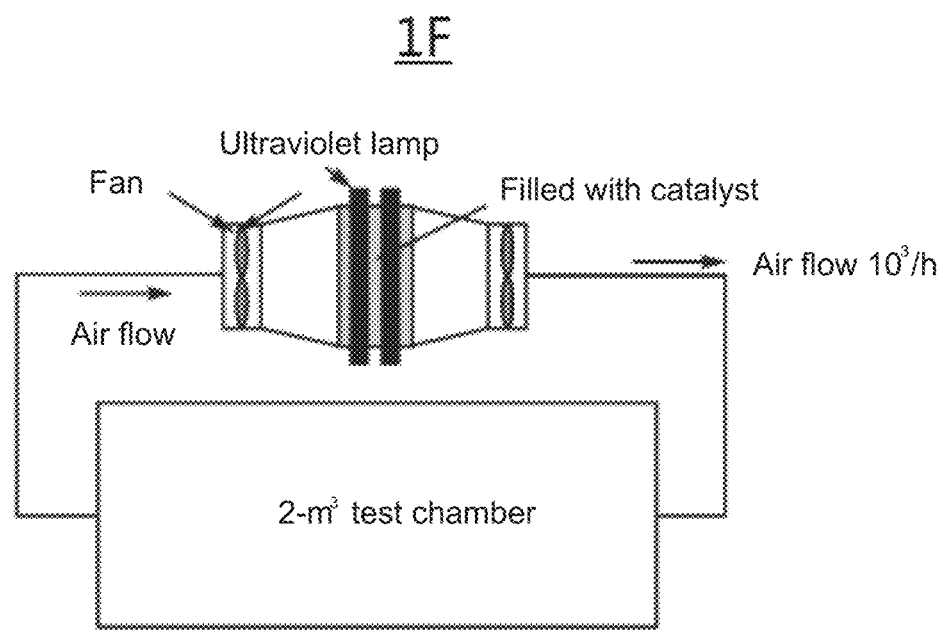
FIG. 6 is a schematic diagram illustrating another photocatalyst apparatus of a light-source-extended type (using $SiO_2$ as a carrier of a photocatalyst) in the prior art.
Figure 7:
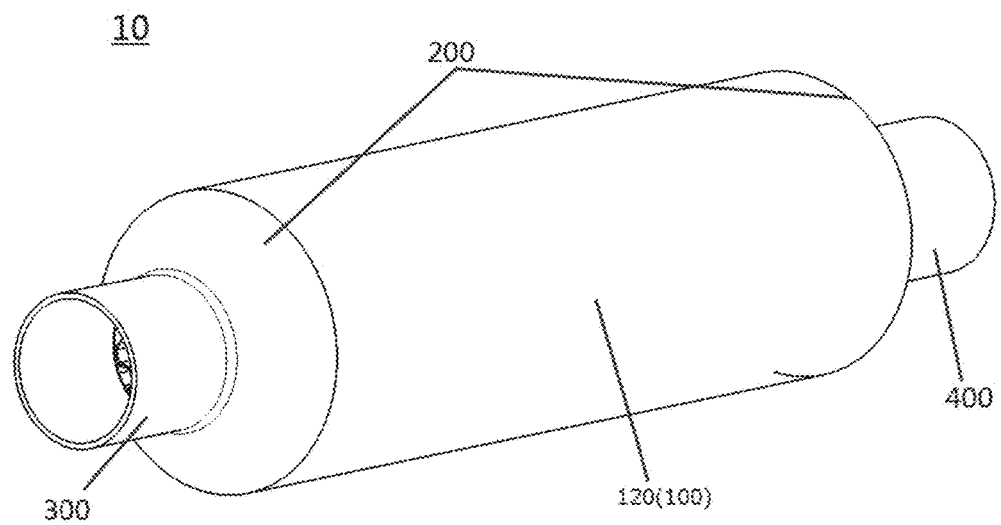
FIG. 7 is a schematic structural diagram illustrating a pipe-type photocatalytic purification apparatus according to the present invention.

First, the overall structure of the photocatalytic purification apparatus 10 according to the present invention is described with reference to FIG. 7. FIG. 7 is a schematic structural diagram illustrating the pipe-type photocatalytic purification apparatus 10 according to the present invention.

As shown in FIG. 7, the pipe-type photocatalytic purification apparatus 10 according to the present invention consists of the photocatalytic honeycomb assembly 100, a side casing 200, an air vent inlet pipe 300 and an air vent outlet pipe 400. Polluted air that contains organic matter, bacteria, viruses, etc. enters the photocatalytic honeycomb assembly 100 of the photocatalytic purification apparatus 10 from the air vent inlet pipe 300 of the photocatalytic purification apparatus 10. Light (for example, ultraviolet light or visible light) emitted by point light sources L1 (referring to FIG. 19) and light strips L2a to L2c (referring to FIG. 20) disposed inside the side casing 200 or light (for example, ultraviolet light or visible light) emitted by a dot-matrix light source L3 (referring to FIG. 14) disposed on an end surface of a light guide member 115') emitted into the photocatalytic honeycomb assembly 100 is used to activate a photocatalyst (for example, $TiO_2$) sprayed and attached onto the photocatalytic honeycomb assembly 100. In this way, the organic matter, bacteria, viruses, etc. contained in the polluted air are decomposed into carbon dioxide and water, that is, to purify the polluted air, and the purified air is then discharged from the air vent outlet pipe 400 of the photocatalytic purification apparatus 10.

(Basic Structure (Basic Implementation Manner) of the Photocatalytic Honeycomb Assembly 100

Figure 8:
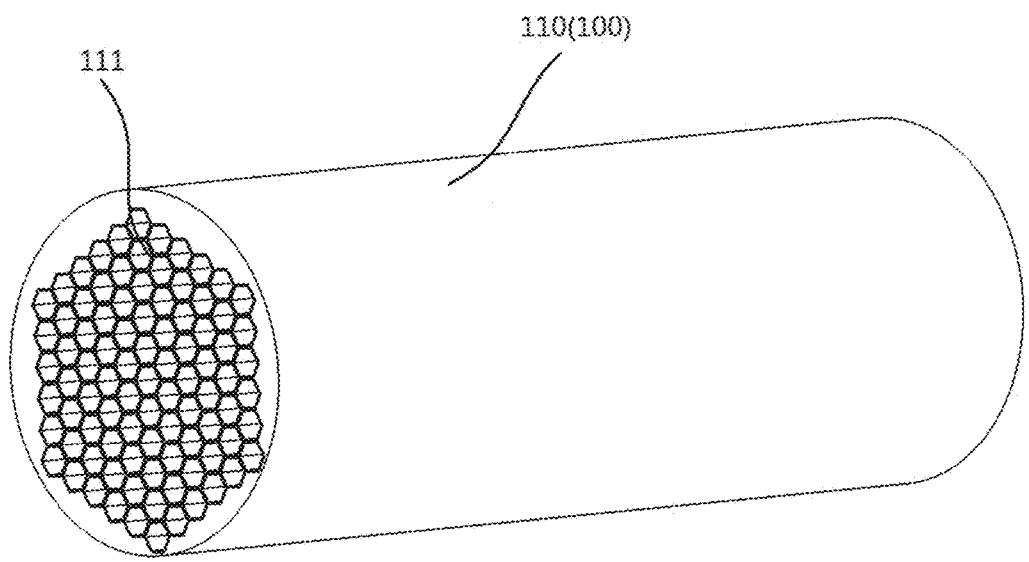
FIG. 8 is a schematic structural diagram illustrating a photocatalytic honeycomb assembly used in the pipe-type photocatalytic purification apparatus according to the present invention.
Figure 9:
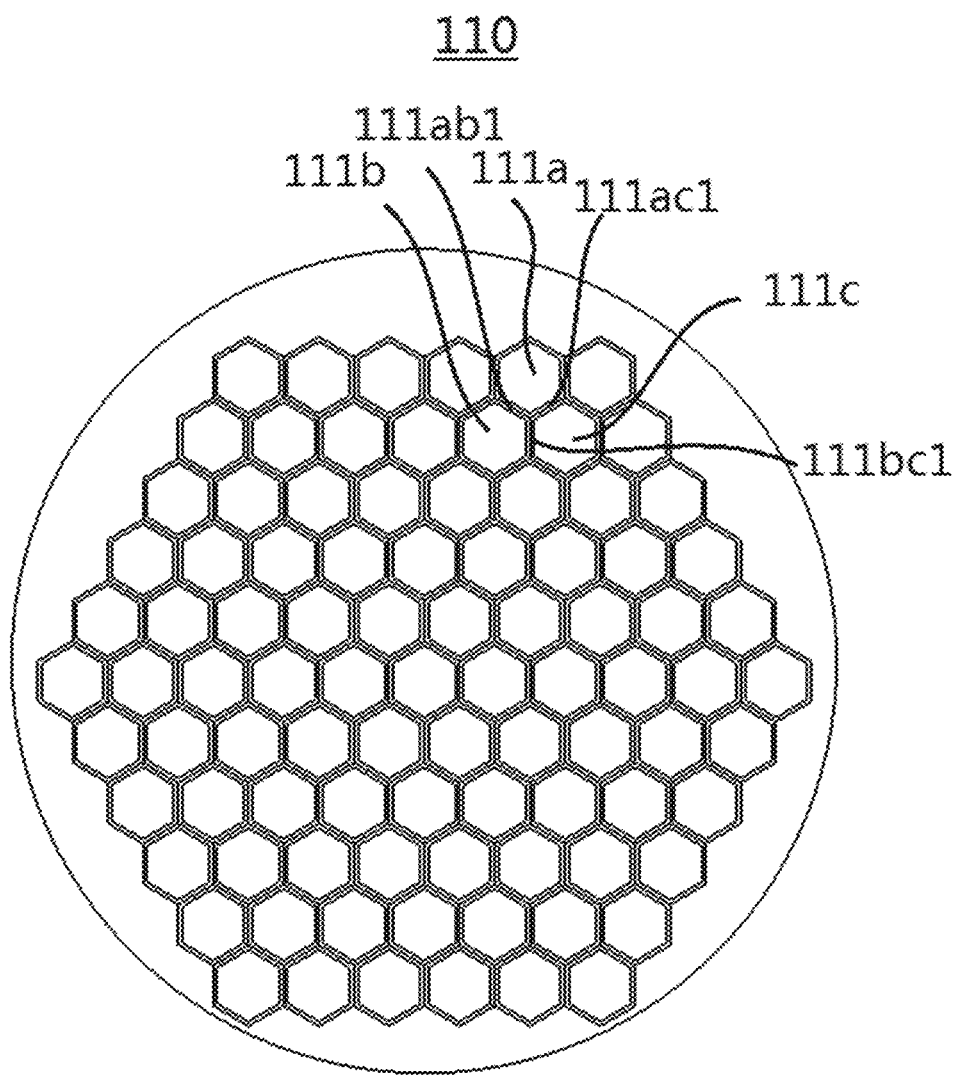
FIG. 9 is a sectional end view illustrating the photocatalytic honeycomb assembly shown in FIG. 8.

Next, with reference to FIG. 7 in conjunction with FIG. 8 and FIG. 9, the basic structure of the photocatalytic honeycomb assembly 100 of the photocatalytic purification apparatus 10 according to the present invention is described. FIG. 8 is a schematic structural diagram illustrating a photocatalytic honeycomb core 110 in the photocatalytic honeycomb assembly 100 used in the pipe-type photocatalytic purification apparatus 10 according to the present invention. FIG. 9 is a sectional end view illustrating the photocatalytic honeycomb core 110 in the photocatalytic honeycomb assembly 100 shown in FIG. 8.

As shown in FIG. 7 and FIG. 8, the photocatalytic honeycomb assembly 100 of the photocatalytic purification apparatus 10 according to the present invention comprises a photocatalytic honeycomb assembly housing 120 and one or more photocatalytic honeycomb cores 110, but the present invention is not limited thereto. Alternatively, the photocatalytic honeycomb assembly 100 of the photocatalytic purification apparatus 10 according to the present invention may also consist of only one or more photocatalytic honeycomb cores 110 and a photocatalytic honeycomb assembly housing 120.

As shown in FIG. 8 and FIG. 9, the photocatalytic honeycomb core 110 is arranged in a honeycomb form. That is, the photocatalytic honeycomb core 110 is formed of multiple basic core units 111 that is hexagonal in an end view in a honeycomb arrangement. Six side surfaces (as shown in FIG. 9, being six lines when observed along an end-view direction) of each basic core unit 111 are joined to or coplanar with side surfaces of six adjacent and different basic core units 111 that are hexagonal in an end view. More specifically, for example, as shown in FIG. 9, when observed along an end-view direction, a hexagonal basic core unit 111a and an adjacent hexagonal basic core unit 111b of the photocatalytic honeycomb core 110 share one side 111ab1, the hexagonal basic core unit 111a and another adjacent hexagonal basic core unit 111c share one side 111ac1, . . . , thus forming the structure of the photocatalytic honeycomb core 110 shown in FIG. 8 and FIG. 9. In addition, a region enclosed by respective coated surfaces (six inner surfaces) of each basic core unit 111 becomes a hexagonal air channel (or channel) 112 through which air can flow.

A photocatalyst (for example, $TiO_2$) coating is sprayed and attached onto the coated surface of the photocatalytic honeycomb core 110, so that a contact surface area between air and a photocatalyst can be increased, while flow resistance to air is reduced, so that pressure loss of equipment is relatively small.

In addition, because the photocatalytic honeycomb core 110 can be configured to be relatively long in an axial direction of the photocatalytic honeycomb assembly 100, a total contact area between air and the photocatalyst can be increased while a diameter of the photocatalytic honeycomb core 110 remains unchanged. Therefore, the photocatalytic honeycomb assembly 100 is particularly applicable to arrangement in an aircraft that has a relatively compact installation space.

(Embodiment 1 of Photocatalytic Honeycomb Assembly 100)

Figure 10:
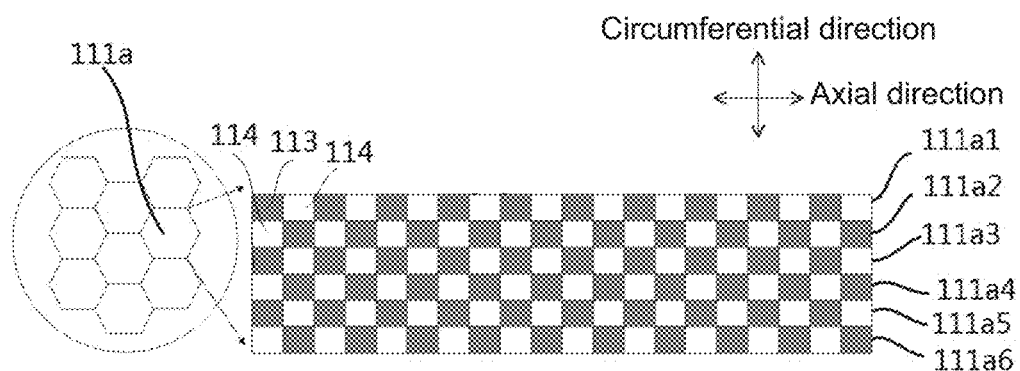
FIG. 10 is a spread view illustrating an embodiment of a photocatalytic honeycomb core in the photocatalytic honeycomb assembly shown in FIG. 9.
Figure 11:
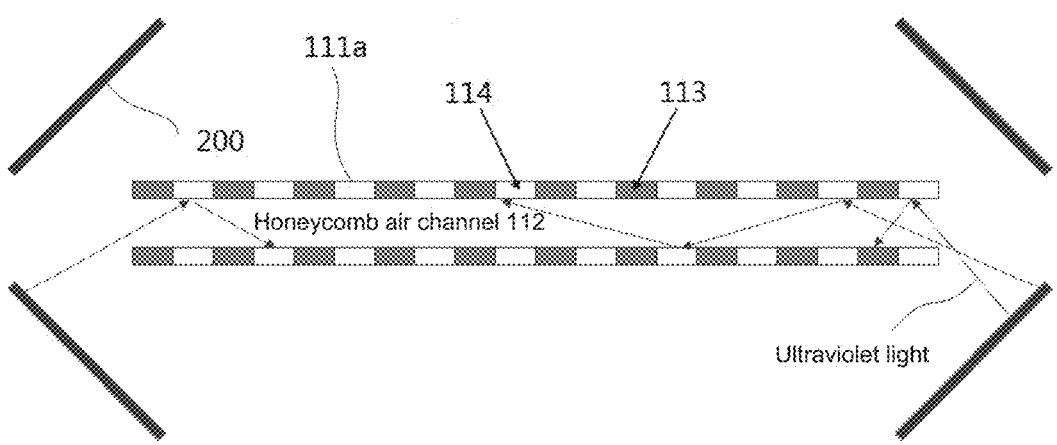
FIG. 11 is a diagram illustrating reflection of light in a hexagonal air channel of a photocatalytic honeycomb core in the photocatalytic honeycomb assembly shown in FIG. 8.

Referring to FIG. 10 and FIG. 11, Embodiment 1 of the photocatalytic honeycomb assembly 100 according to the present invention is described. FIG. 10 is a spread view illustrating an embodiment of the photocatalytic honeycomb core 110 in the photocatalytic honeycomb assembly 100 shown in FIG. 9. FIG. 11 is a diagram illustrating reflection of light in the hexagonal air channel 112 of the photocatalytic honeycomb core 110 in the photocatalytic honeycomb assembly 100 shown in FIG. 8.

Just as discussed in the analysis of the prior art in the background art, in consideration of a limited irradiation range of a light source, there is a problem that the light source cannot effectively irradiate light to the interior of the photocatalytic honeycomb core 110. The longer the length of the photocatalytic honeycomb core 110 in an axial direction of the photocatalytic honeycomb assembly 100 is, the severer the problem is.

In the prior art, to resolve this problem, a honeycomb-channel stacked structure is proposed. However, in this case, air flowing in a hexagonal air channel (channel) is subject to relatively large flow resistance, which probably cannot satisfy flow resistance requirements in the field of ventilation systems that are relatively sensitive to flow resistance, for example, a ventilation system for a vehicle.

Therefore, in Embodiment 1, a method distinct from that in the prior art is used to resolve the foregoing problem. The use of an arrangement in which a specular reflection coating and a photocatalyst coating are alternately distributed on the coated surfaces of the basic core units 111 in the photocatalytic honeycomb core 110 is considered.

More specifically, as shown in FIG. 10, in a spread view in which a basic core unit 111a of the photocatalytic honeycomb core 110 in the photocatalytic honeycomb assembly 100 is spread, six rows of regions along the axial direction (a transverse direction in FIG. 10) represent six inner surfaces (coated surfaces) 111a1, 111a2, 111a3, 111a4, 111a5, and 111a6 of the basic core unit 111a that is hexagonal in an end view. Next, six coated surfaces of the basic core unit 111a are divided along a circumferential direction (a longitudinal direction in FIG. 10) at regular intervals. In this way, each coated surface is divided into rectangular (for example, square) regions (alternately disposed regions) that have equal areas. Then, different coatings are sprayed and attached to individual rectangular regions that are adjacent in the axial direction (the transverse direction) and the circumferential direction (the longitudinal direction). For example, a photocatalyst coating 113 is sprayed and attached onto a rectangular region, a specular reflection coating 114 is sprayed and attached onto a rectangular region adjacent to the former rectangular region along the axial direction, and the specular reflection coating 114 is also sprayed and attached onto a rectangular region adjacent to the former rectangular region along the circumferential direction.

In this way, as shown in FIG. 11 illustrating reflection of light in the hexagonal air channel 112, in the hexagonal air channel 112 enclosed by six coated surfaces of the basic core unit 111a that is hexagonal in an end view, light (for example, ultraviolet light or visible light) emitted by the point light source L1 (referring to FIG. 19), the light strips L2a to L2c (referring to FIG. 20), etc. disposed inside the side casing 200 is reflected inside the photocatalytic honeycomb core 110 by the specular reflection coating 114 along the axial direction of the photocatalytic honeycomb assembly 100. Light can be irradiated to even a position in the center of the hexagonal air channel 112 of the photocatalytic honeycomb core 110 that has a relatively long axial length. In this way, the specular reflection coating 114 can alternately reflect light (for example, ultraviolet light or visible light) emitted by the point light sources L1 (referring to FIG. 19), the light strips L2a to L2c (referring to FIG. 20), etc. disposed on the side casing 200 on two sides of the photocatalytic honeycomb core 110 into the hexagonal air channel 112. The photocatalyst coating is irradiated with ultraviolet light that is reflected one or more times by the specular reflection coating, so that the photocatalyst is activated to decompose organic matter, bacteria, viruses, etc. contained in polluted air into carbon dioxide and water, that is, to purify the polluted air.

(A Variant of Embodiment 1 of Photocatalytic Honeycomb Assembly 100)

Figure 12:
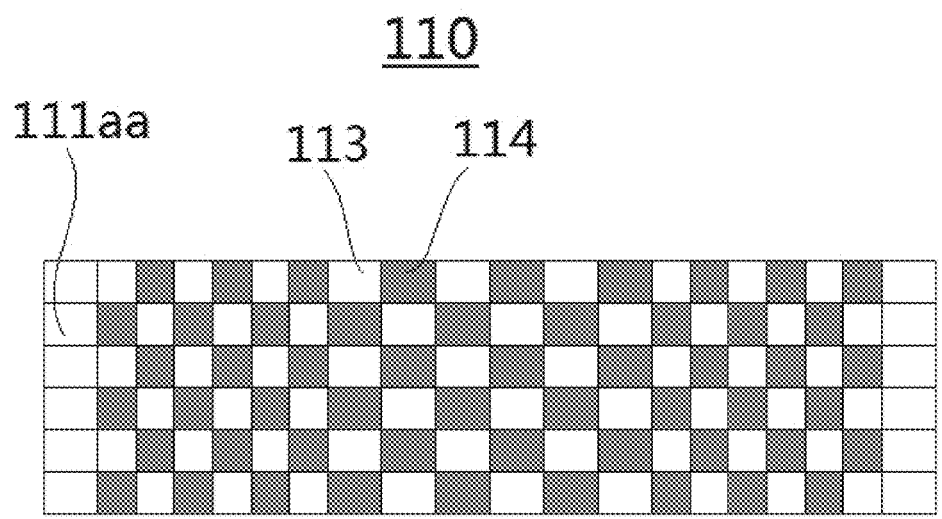
FIG. 12 is a spread view illustrating a variant embodiment of a photocatalytic honeycomb core in the photocatalytic honeycomb assembly shown in FIG. 9.

Referring to FIG. 12, Embodiment 1 of the photocatalytic honeycomb assembly 100 according to the present invention is described. FIG. 12 is a spread view illustrating the photocatalytic honeycomb core 110 in the photocatalytic honeycomb assembly 100 shown in FIG. 9. FIG. 12 is a spread view illustrating a variant embodiment of the photocatalytic honeycomb core 110 in the photocatalytic honeycomb assembly 100 shown in FIG. 9.

A difference between this variant embodiment and Embodiment 1 described above lies in that, in the foregoing Embodiment 1, as shown in FIG. 10, each coated surface is divided along the circumferential direction (the longitudinal direction in FIG. 10) at regular intervals into rectangular (for example, square) regions (alternately disposed regions) that have equal areas. However, in this variant embodiment, as shown in FIG. 12, each coated surface is divided along the circumferential direction (the longitudinal direction in FIG. 12) at irregular intervals into rectangular regions (alternately disposed regions) that have different areas.

More specifically, as shown in FIG. 12, ultraviolet light on two end sides (that is, end sides near the side casing 200) of the hexagonal air channel 112 (referring to FIG. 11) is of relatively high intensity, and ultraviolet light in a central region in an axial direction (that is, the position in the center of the hexagonal air channel 112) is of relatively low intensity. Therefore, each coated surface is divided along the circumferential direction (the longitudinal direction in FIG. 12) in such a manner that area of those near the two end sides of the hexagonal air channel 112 are smaller and the area of those near the central region in the axial direction are larger. Different coatings (the photocatalyst coating 113 or the specular reflection coating 114) are sprayed and attached onto individual rectangular regions that are adjacent in the axial direction (the transverse direction) and the circumferential direction (the longitudinal direction).

In addition, an outermost region of the two end sides of the hexagonal air channel 112 is configured to be a specular reflection coating region 111aa that has a relatively large area, and the specular reflection coating 114 is sprayed and attached onto the specular reflection coating region 111aa.

By using the structure discussed above, light of light sources can be maximally guided inside, so that light of greater intensity in the outermost region on the two end sides of the hexagonal air channel 112 is not excessively absorbed.

(Embodiment 2 of Photocatalytic Honeycomb Assembly 100)

Figure 13:
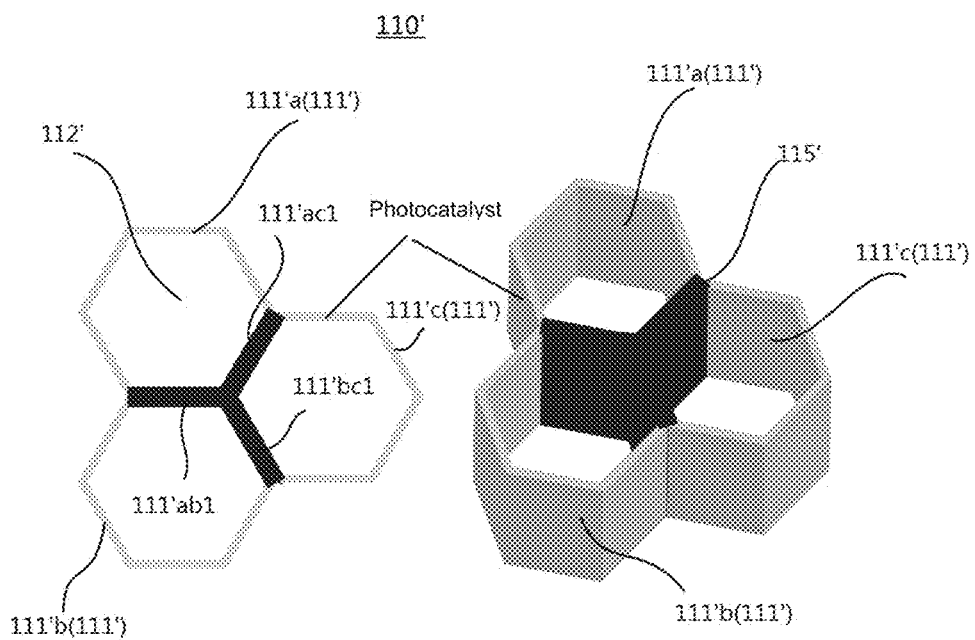
FIG. 13 is a partial schematic diagram illustrating a variant embodiment "Embodiment 2" of a photocatalytic honeycomb assembly used in a pipe-type photocatalytic purification apparatus according to the present invention, and shows a part of a photocatalytic honeycomb core in the photocatalytic honeycomb assembly.
Figure 14:
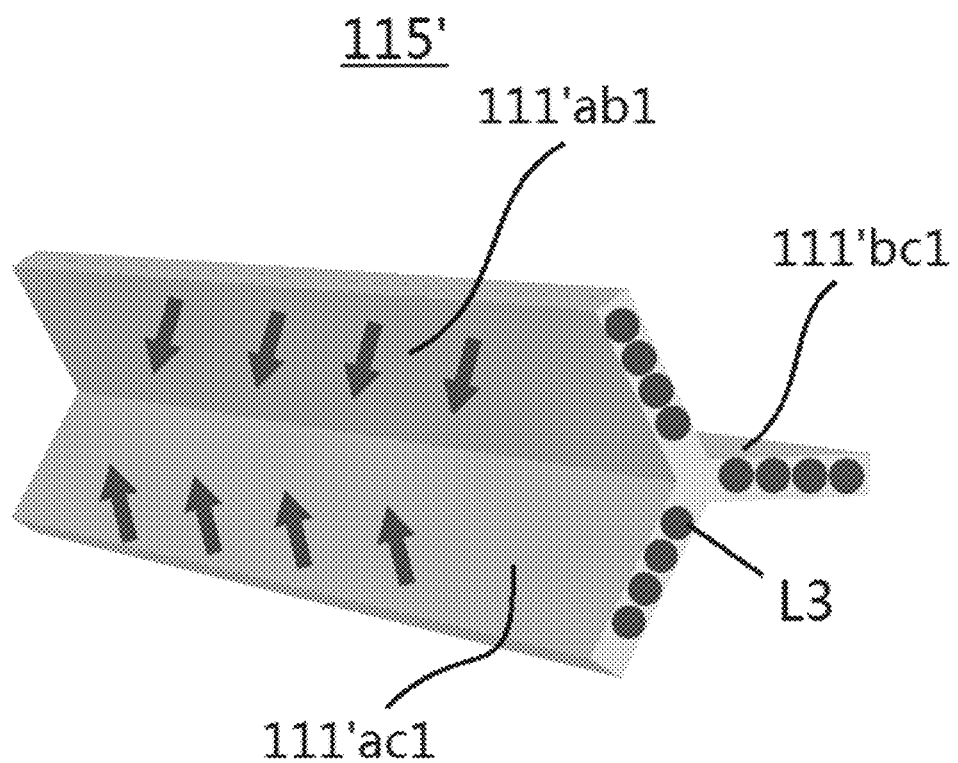
FIG. 14 is a schematic diagram illustrating a light guide member in the photocatalytic honeycomb core shown in FIG. 13.

Next, referring to FIG. 13 and FIG. 12, Embodiment 2 of the photocatalytic honeycomb assembly 100 according to the present invention is described. FIG. 13 is a partial schematic diagram illustrating Embodiment 2 of the photocatalytic honeycomb assembly 100 used in the pipe-type photocatalytic purification apparatus 10 according to the present invention, and shows a part of the photocatalytic honeycomb core 110' of the photocatalytic honeycomb assembly 100. FIG. 14 is a schematic diagram illustrating the light guide member 115' in the s photocatalytic honeycomb core 110' shown in FIG. 13.

A difference between Embodiment 2 and the foregoing Embodiment 1 lies in that, in the foregoing Embodiment 1, as shown in FIG. 10, each basic core unit 111 is formed of six coated surfaces. Multiple basic core units 111 are configured in a honeycomb form, so as to form the photocatalytic honeycomb core 110. However, in Embodiment 2, as shown in FIG. 13, the light guide member 115' is disposed among every three basic core units 111' (111'a, 111'b, 111'c) that are adjacent to one another, and each basic core unit 111' (111'a, 111'b, 111'c) is formed of four coated surfaces and two light guide surfaces of the light guide member 115'. In addition, a difference between Embodiment 2 and the foregoing Embodiment 1 lies in that, in the foregoing Embodiment 1, the light sources (the point light sources L1 (referring to FIG. 19) and the light strips L2a to L2c (referring to FIG. 20)) are disposed on the side casing 200 on the two sides of the photocatalytic honeycomb core 110. However, in Embodiment 2, the light sources (the dot-matrix light source L3) are disposed on an end surface of the light guide member 115'. Therefore, the description is mainly about differences between Embodiment 2 and Embodiment 1, while the same parts are referred to with the same or corresponding reference numerals, and detailed descriptions of the same parts are omitted.

More specifically, in the photocatalytic honeycomb core 110' of the photocatalytic honeycomb assembly 100 in Embodiment 2, as shown in FIG. 13, a group of three basic core units 111'a, 111'b, and 111'c that are adjacent to one another is taken as an example for description. Among the three basic core units 111'a, 111'b, and 111'c, a first basic core unit 111'a and a second basic core unit 111'b share a plate body (a light guide plate 111'ab1 shown in FIG. 13), the first basic core unit 111'a and a third basic core unit 111'c share a plate body (a light guide plate 111'ac1 shown in FIG. 13), and the second basic core unit 111'b and the third basic core unit 111'c share a plate body (a light guide plate 111'bc1 shown in FIG. 13). In FIG. 13, the three light guide plates 111'ab1, 111'ac1, and 111'bc1 form the light guide member 115' that is Y-shaped in an end view in Embodiment 2. In this way, a form of a hexagonal air channel 112' that is formed of four coated surfaces and two light guide surfaces of the light guide plates and through which air can flow is used in each of the basic core units 111'a, 111'b, and 111'c.

In addition, as shown in FIG. 14, a row of multiple (a row of four in FIG. 13, on end surfaces of the three light guide plates 111'ab1, 111'ac1, and 111'bc, 12 in total in three rows) dot-matrix light sources L3 are disposed on an end surface of each of the light guide plates 111'ab1, 111'ac1, and 111'bc1 of the light guide member 115' that is Y-shaped in an end view. The dot-matrix light sources L3 extend along an axial length of the photocatalytic honeycomb core 110' and are configured inside the light guide plates 111'ab1, 111'ac1, and 111'bc. By using the light guide member 115' (the light guide plates 111'ab1, 111'ac1, and 111'bc1), light emitted by the dot-matrix light sources L3 installed on the end surfaces and extending and configured along an axial length of the photocatalytic honeycomb core 110 is guided to the hexagonal air channels 112' of the basic core units 111'.

In addition, as shown in FIG. 13, in Embodiment 2, the photocatalyst coating 113 is sprayed and attached onto the four coated surfaces.

By using the structure discussed above, the photocatalyst coating 113 sprayed and attached onto the coated surfaces of each basic core unit can receive uniform light irradiation, so as to set off uniform and ideal photocatalytic purification reactions.

Certainly, it is also possible to be similar to that in Embodiment 1, such that the coated surface may be divided at regular intervals or at irregular intervals into multiple rectangular regions (alternately disposed regions) that have same areas or different areas, and the photocatalyst coating 113 and the specular reflection coating 114 (referring to FIG. 10) are alternately sprayed and attached onto the rectangular regions. In this way, not only is the light guide member 115' used to transform light emitted by light sources (the dot-matrix light sources L3) into a surface light source facing the hexagonal air channel 112' of the basic core unit 111', but also the specular reflection coating 114 can be used to make light irradiation on the hexagonal air channel 112' of the basic core unit 111' more uniform.

(Embodiment 3 of Photocatalytic Honeycomb Assembly 100)

Figure 15:
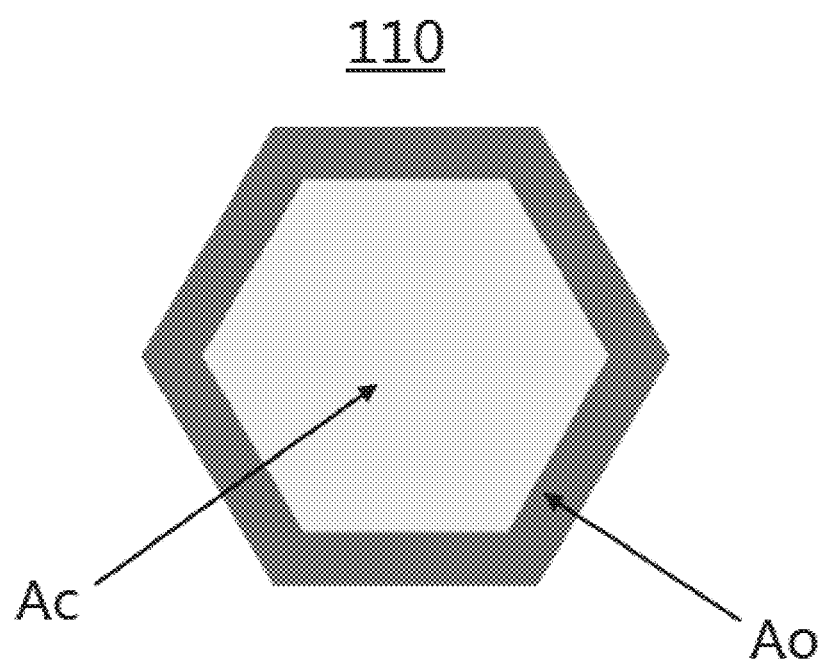
FIG. 15 is a schematic diagram illustrating an air flow in a hexagonal air channel of a photocatalytic honeycomb core in the photocatalytic honeycomb assembly shown in FIG. 9.
Figure 16:
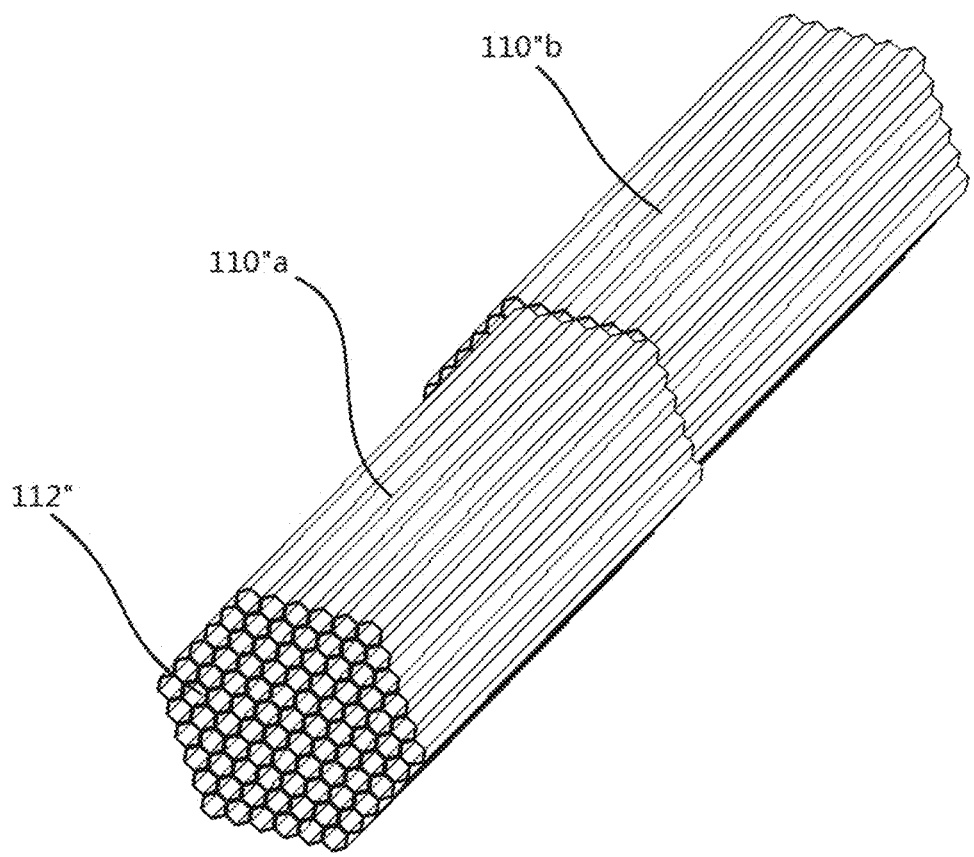
FIG. 16 is a schematic diagram illustrating a variant embodiment "Embodiment 3" of a photocatalytic honeycomb assembly used in a pipe-type s photocatalytic purification apparatus according to the present invention, and shows a form in which multiple photocatalytic honeycomb cores of the photocatalytic honeycomb assembly are configured in a misaligned manner.
Figure 17:
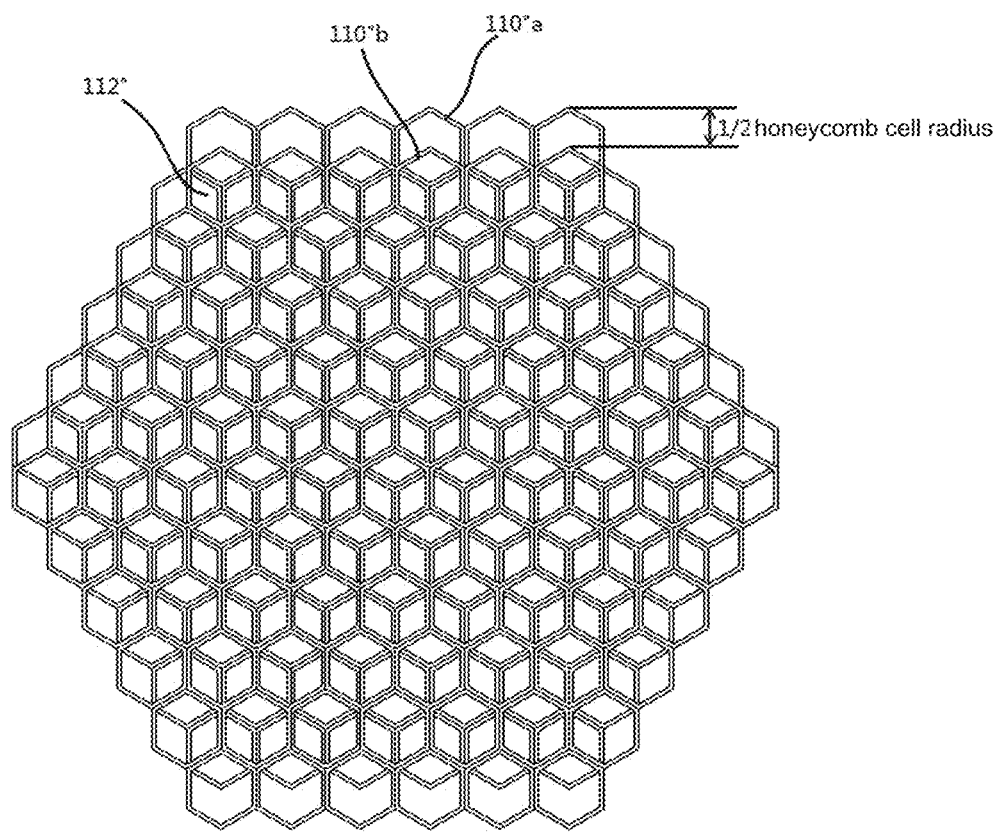
FIG. 17 is a diagram illustrating an intersecting surface of the multiple photocatalytic honeycomb cores shown in FIG. 16 observed in an end-view direction.
Figure 18:
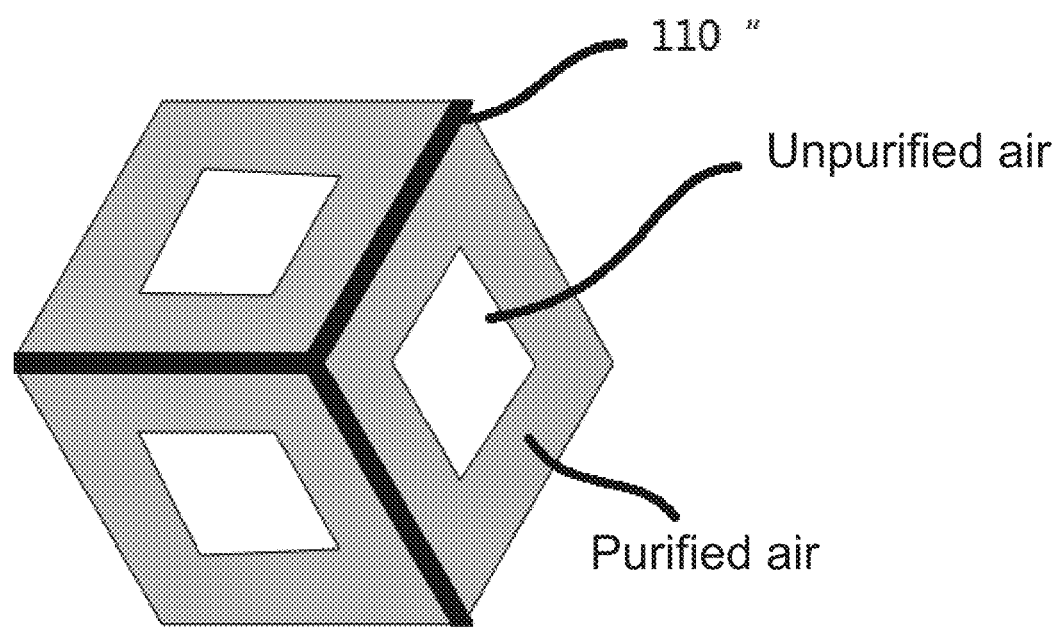
FIG. 18 is a schematic diagram illustrating an air flow in a hexagonal air channel of the photocatalytic honeycomb core in the photocatalytic honeycomb assembly shown in FIG. 16 in another variant embodiment.

Next, referring to FIG. 15 and FIG. 16, Embodiment 3 of the photocatalytic honeycomb assembly 100 according to the present invention is described. FIG. 15 is a schematic diagram illustrating an air flow in the hexagonal air channel 112 of the photocatalytic honeycomb core 110 in the photocatalytic honeycomb assembly 100 shown in FIG. 9. FIG. 16 is a schematic diagram illustrating Embodiment 3 of the photocatalytic honeycomb assembly 100 used in the pipe-type photocatalytic purification apparatus 10 according to the present invention, and shows a form in which multiple photocatalytic honeycomb cores 110"a and 110"b of the photocatalytic honeycomb assembly 100 are configured in a misaligned manner. FIG. 17 is a diagram illustrating an intersecting surface of the multiple photocatalytic honeycomb cores 110"a and 110"b shown in FIG. 16 observed in an end-view direction. FIG. 18 is a schematic diagram illustrating an air flow in the hexagonal air channel 112" of the photocatalytic honeycomb core 110" in the photocatalytic honeycomb assembly 100 of Embodiment 3.

When compared with the foregoing Embodiment 1 and Embodiment 2, differences of Embodiment 3 lie in that, in the foregoing Embodiment 1 and Embodiment 2, the multiple photocatalytic honeycomb cores 110" are configured to be joined to each other in an aligned manner, so as to form the hexagonal air channel 112, however, in Embodiment 3, as shown in FIG. 16, the multiple photocatalytic honeycomb cores 110"a and 110"b are configured to be joined in a manner of being misaligned with each other by ½ of a honeycomb cell radius. In this way, the hexagonal air channel 112" on an intersecting surface of the photocatalytic honeycomb core 110"a and 110"b is cut into three rhombuses (quadrilaterals).

In the photocatalytic honeycomb core 110 in the photocatalytic honeycomb assembly 100 in the basic implementation, as shown in FIG. 15, a peripheral part Ao of an air flow passing through the hexagonal air channel 112 (an air flow near a coated surface of a basic core unit) is thoroughly purified under the catalytic effect of a photocatalyst sprayed and attached onto a photocatalyst coating. However, a central part Ac of the air flow is not fully exposed to the photocatalyst and therefore may not be thoroughly purified.

In Embodiment 3, a specific configuration is shown in FIG. 16 in which the multiple photocatalytic honeycomb cores 110"a and 110"b are configured to be joined in a manner of being misaligned with each other by ½ of the honeycomb cell radius. An intersecting surface of the multiple photocatalytic honeycomb cores in the joined configuration is shown in FIG. 17 as observed in an end-view direction.

As shown in FIG. 17, when air flows from one photocatalytic honeycomb core 110"a to another photocatalytic honeycomb core 110"b, because the photocatalytic honeycomb core 110"a and the photocatalytic honeycomb core 110"b are misaligned with each other by ½ of the honeycomb cell radius, the hexagonal air channel 112" on an intersecting surface of the two photocatalytic honeycomb cores 110"a and 110"b is cut into three rhombuses (quadrilaterals) from the original hexagon. In this way, the contact area between the air and the photocatalyst coatings can be increased, thereby improving the uniformity of the catalytic reaction.

As may be known by comparing FIG. 18 with FIG. 16, the amount of thoroughly purified air can be greatly increased, and the amount of air that may not be thoroughly purified is obviously reduced.

In addition, Embodiment 3 may be combined with Embodiment 1 and Embodiment 2 to create a new embodiment.

(Embodiment of Side Casing 200)

Figure 19:
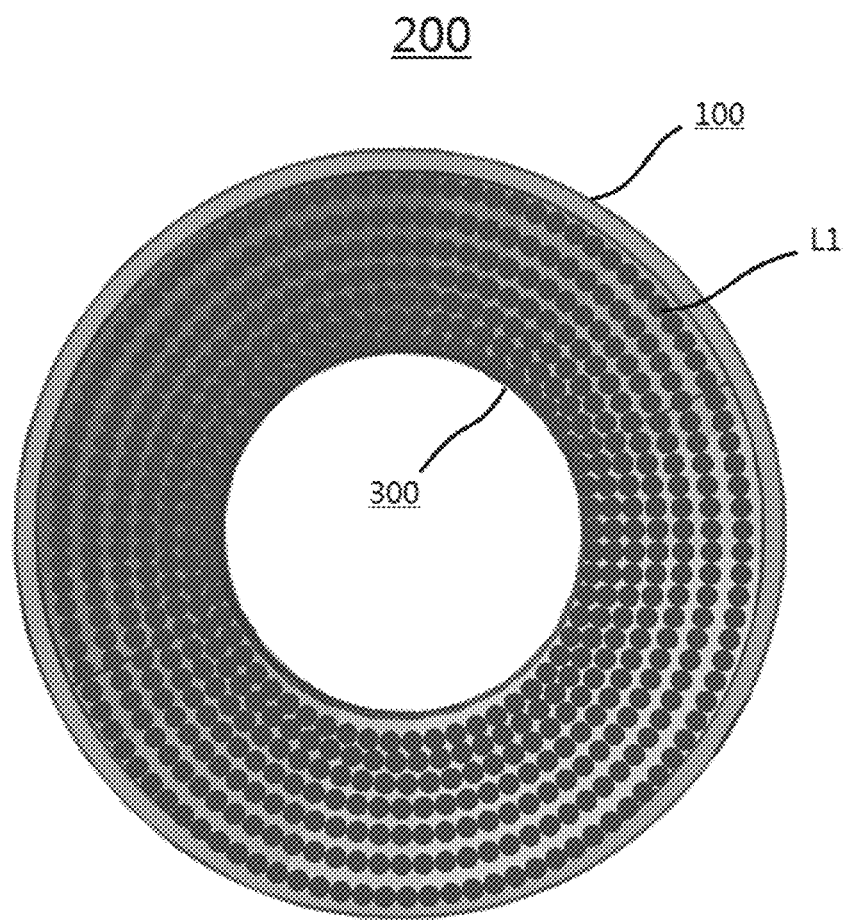
FIG. 19 is a schematic diagram illustrating a side casing used in the pipe-type photocatalytic purification apparatus shown in FIG. 7.

In the following, an embodiment of the side casing 200 of the pipe-type photocatalytic purification apparatus 10 according to the present invention is described. FIG. 19 is a schematic diagram illustrating the side casing used in the pipe-type photocatalytic purification apparatus 10 shown in FIG. 7.

As shown in FIG. 7, one end of the side casing 200 is connected to a port of the air vent inlet pipe 300 or the air vent outlet pipe 400, and the other end thereof is connected to the photocatalytic honeycomb assembly 100. The inner diameter of the side casing 200 gradually increases from one end (on the side near the port of the air vent inlet pipe 300 or the air vent outlet pipe 400) towards the other end (on the side near the photocatalytic honeycomb assembly 100) of the side casing 200.

Inside (on an inner side surface of) the side casing 200, multiple point light sources L1 are disposed in the form of concentric circles. In this way, light emitted by the multiple point light sources L1 is irradiated into the photocatalytic honeycomb core 110 of the photocatalytic honeycomb assembly 100.

A part (a first light source section) located on an inner surface on one end side of the side casing has the lowest light intensity, and another part (a third light source section) located on an inner surface on the other end side of the side casing has the highest light intensity. Light intensity in a second light source section located between the first light source section and the third light source section ranges between the intensity of the first light source section and the intensity of the third light source section.

In a high purification mode, the first light source section, the second light source section, and the third light source section are all turned on. In a medium purification mode, the first light source section and the second light source section are turned on. In a low purification mode, only the first light source section is turned on.

By using the structure discussed above, light emitted by light sources with different intensity can be used to meet purification requirements of different processing demands.

(Variant Embodiment of Side Casing 200)

Figure 20:
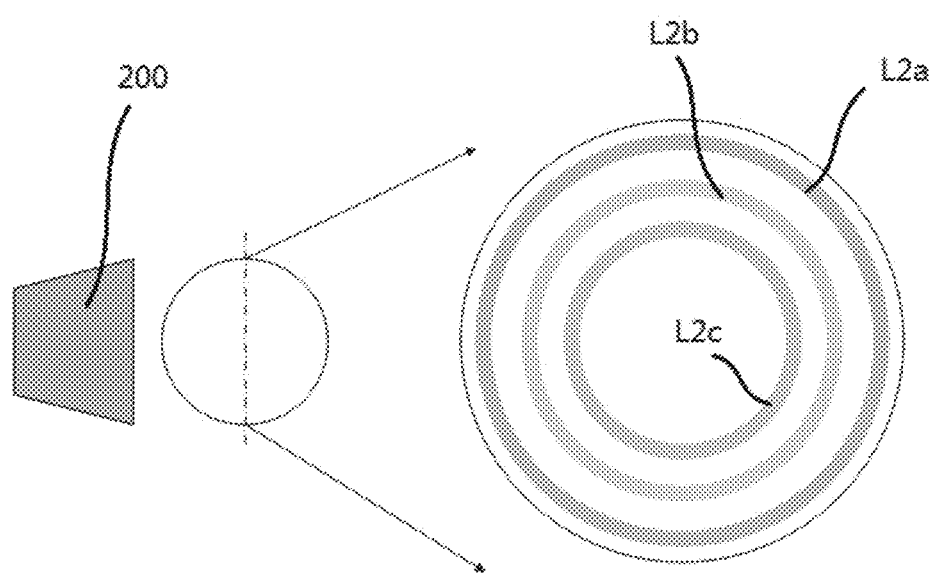
FIG. 20 is a schematic diagram illustrating a variant embodiment of a side casing used in the pipe-type photocatalytic purification apparatus shown in FIG. 7.

In the following, a variant embodiment of the side casing 200 of the pipe-type photocatalytic purification apparatus 10 according to the present invention is described. FIG. 20 is a schematic diagram illustrating a variant embodiment of the side casing used in the pipe-type photocatalytic purification apparatus 10 shown in FIG. 7.

Compared with the embodiment of the side casing 200, as shown in FIG. 20, three light strips L2a to L2c disposed in the form of concentric circles are used in the variant embodiment of the side casing 200. The light intensity (diameter) of the first light strip L2a located on an inner surface on one end side of the side casing 200 is the smallest, and the light intensity (diameter) of the third light strip L2c located on an inner surface on the other end side of the side casing 200 is the greatest.

In the high purification mode, the three light strips L2a to L2c are all turned on. In the medium purification mode, the first light strip L2a and the second light strip L2b are turned on. In the low purification mode, only the first light strip L2a is turned on.

By using the structure discussed above, light emitted by light sources with different intensity can also be used to meet purification requirements of different processing demands.

A person skilled in the art can easily conceive of other advantages and modifications. Therefore, on a broader sense, the present invention is not limited to specific details and representative embodiments shown and described herein. Therefore, modifications may be made without departing from the spirit or scope of the general inventive concept as defined by the appended claims and equivalents thereof.

For example, in the foregoing Embodiment 1, Embodiment 3 and the variant embodiments thereof, a photocatalyst coating and a specular reflection coating are attached onto six inner surfaces of each basic core unit, but the present invention is not limited thereto. Alternatively, it is also possible that only the photocatalyst coating is attached onto some or all of the six inner surfaces of each basic core unit, and on the remaining inner surfaces, other coatings are not attached thereto or required coatings other than the specular reflection coating are attached thereto. In this way, the following technical effects of the present invention can also be achieved, that is, a contact surface area between air flow and a photocatalyst can be increased, while flow resistance to air is reduced, and pressure loss of equipment is relatively small.

In addition, in the foregoing Embodiment 1, Embodiment 3 and the variant embodiments thereof, the cases where each basic core unit is in the shape of a hexagon (or a regular hexagon) in an end view are exemplified, but the present invention is not limited thereto. The shape of each basic core unit in an end view may be a polygon, including a triangle, a quadrilateral, a pentagon and a hexagon, wherein the polygon may be a regular polygon or may not be a regular polygon. In addition, the shape of each basic core unit in an end view may alternatively be a round shape including a circle and an ellipse. In addition, the shape of each basic core unit in an end view may further be a shape combining a polygon and a round shape, including an elongated round shape (that is, a shape of which two sides are straight lines and two ends are round).

For example, in the foregoing Embodiment 1, the embodiments and the variants of the embodiments, different coatings, that is, a photocatalyst coating and a specular reflection coating are alternately sprayed and attached onto the adjacent alternately disposed regions in the axial direction and the circumferential direction, but the present invention is not limited thereto. After light rays are transferred inside a core, light intensity attenuates along the axial direction. Therefore, the technical effects of the present invention can basically be achieved by only alternately spraying and attaching different coatings in the axial direction. That is, ultraviolet light can be irradiated to even a position in the center of the hexagonal air channel of the photocatalytic honeycomb core that has a long axial length.

In addition, if different coatings, that is, a photocatalyst coating and a specular reflection coating, are also alternately sprayed and attached in the alternately disposed regions that are adjacent in the circumferential direction in addition to the axial direction, light (for example, ultraviolet light or visible light) emitted by point light sources, light strips, etc. that are disposed inside the side casing can be reflected more uniformly inside the photocatalytic honeycomb core, so as to avoid a case in which the catalytic efficiency of some photocatalyst coatings inside the photocatalytic honeycomb core is significantly reduced as compared with the catalytic efficiency of photocatalyst coatings in other parts.

For example, in the variant embodiment of the side casing 200, three light strips L2a to L2c are formed, but the present invention is not limited thereto. Provided that at least two light strips are disposed, intelligent adjustment of purification capability according to different treatment requirements (purification modes) can be implemented.

For example, in the foregoing embodiments and variants, for the light sources, examples of the multiple point light sources L1 (referring to FIG. 19) disposed on the side casing 200 in the form of concentric circles, three (multiple) light strips (referring to FIG. 20) disposed on the side casing 200 in the form of concentric circles, and the dot-matrix light sources L3 disposed on an end surface of the light guide member 115' are enumerated. However, it is conceivable to a person skilled in the art that even if light sources are disposed in a disorderly manner, the present invention can still be implemented. For example, a strip light source formed of the dot-matrix light sources L3 shown in FIG. 13 arranged in one line may be alternatively disposed on an end surface of the light guide member.

For example, in the photocatalytic purification apparatus 10 of the present invention, a case where multiple light sources are provided on the side casing 200 is presented, but the present invention is not limited thereto. Alternatively, there may be only one light source that can emit light being disposed on the side casing 200.

The invention claimed is:

1. A photocatalytic honeycomb assembly, comprising:
a photocatalytic honeycomb assembly housing and one or more photocatalytic honeycomb cores, the photocatalytic honeycomb core being formed of three or more basic core units and a light guide member which are arranged in a honeycomb form, the light guide member being Y-shaped in an end view and being disposed between three basic core units that are adjacent to one another, among the three basic core units that are adjacent to one another, a first basic core unit and a second basic core unit sharing a first light guide plate;

the first basic core unit and a third basic core unit sharing a second light guide plate, and the second basic core unit and the third basic core unit sharing a third light guide plate, each basic core unit being in a form of a honeycomb air channel that is formed of four coated surfaces and two light guide surfaces of the light guide plates and is able to allow air to flow therethrough, and the first light guide plate, the second light guide plate and the third light guide plate forming the light guide member that is able to guide ultraviolet light emitted by light sources into the honeycomb air channels.

2. The photocatalytic honeycomb assembly as claimed in claim 1, wherein a photocatalyst coating is sprayed and attached onto the four coated surfaces of each basic core unit.

3. The photocatalytic honeycomb assembly as claimed in claim 1, the assembly further comprising light sources, wherein the light sources include interior light sources disposed in the photocatalytic honeycomb assembly, the interior light sources are disposed on an end surface of each light guide plate of the light guide member that is Y-shaped in an end view, and the interior light sources extend along an axial length of the photocatalytic honeycomb core and are configured inside the light guide plate.

4. The photocatalytic honeycomb assembly as claimed in claim 3, wherein the light sources disposed on each light guide plate of the light guide member are a row of multiple dot-matrix light sources or strip light sources.

5. The photocatalytic honeycomb assembly as claimed in claim 1, wherein the four coated surfaces of the basic core unit are divided at regular intervals in a circumferential direction of the photocatalytic honeycomb core, so as to divide each of the coated surfaces into multiple rectangular alternately disposed regions of equal areas that are adjacent to one another in both the axial direction and the circumferential direction, different coatings are alternately sprayed and attached onto the alternately disposed regions that are adjacent in the axial direction.

6. The photocatalytic honeycomb assembly as claimed in claim 5, wherein different coatings are also alternately sprayed and attached onto the alternately disposed regions that are adjacent in the circumferential direction.

7. The photocatalytic honeycomb assembly as claimed in claim 1, wherein a photocatalyst coating is sprayed and attached onto one, two or three of the four coated surfaces of each basic core unit, and a specular reflection coating is sprayed and attached onto the remaining coated surfaces.

8. A photocatalytic purification apparatus, wherein the photocatalytic purification apparatus is comprised of a photocatalytic honeycomb assembly as claimed in claim 1, a side casing, an air vent inlet pipe and an air vent outlet pipe, and one or more outer light sources able to emit light are disposed on an inner side surface of the side casing.

9. The photocatalytic purification apparatus as claimed in claim 8, wherein multiple outer light sources are disposed on an inner side surface of the side casing; and the multiple outer light sources are multiple LED point light sources that are arranged on the inner side surface of the side casing in the form of concentric circles, and light emitted from the multiple LED point light sources is irradiated into the photocatalytic honeycomb core of the photocatalytic honeycomb assembly.

10. The photocatalytic purification apparatus as claimed in claim 9, wherein a first light source section or a first light strip located on the inner surface on one end side of the side casing has the lowest light intensity, and a third light source section or a third light strip located on the inner surface on the other end side of the side casing has the highest light intensity, in a high purification mode, the first light source section or first light strip, a second light source section or second light strip, and the third light source section or third light strip are all turned on, in a medium purification mode, the first light source section or first light strip and the second light source section or second light strip are turned on, and in a low purification mode, only the first light source section or first light strip is turned on.

11. The photocatalytic purification apparatus as claimed in claim 8, wherein multiple outer light sources are disposed on an inner side surface of the side casing; and the multiple outer light sources are multiple light strips that are arranged on the inner side surface of the side casing in the form of concentric circles, and light emitted from the multiple light strips is irradiated into the photocatalytic honeycomb core of the photocatalytic honeycomb assembly.

* * * * *